United States Patent
Gilbert et al.

(10) Patent No.: US 10,921,410 B2
(45) Date of Patent: Feb. 16, 2021

(54) METHOD AND SYSTEM FOR SUSCEPTIBILITY WEIGHTED MAGNETIC RESONANCE IMAGING

(71) Applicant: KONINKLIJKE PHILIPS N.V., Eindhoven (NL)

(72) Inventors: Guillaume Gilbert, Eindhoven (NL); Zhaolin Chen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 478 days.

(21) Appl. No.: 15/547,557

(22) PCT Filed: Jan. 29, 2016

(86) PCT No.: PCT/EP2016/051908
§ 371 (c)(1),
(2) Date: Jul. 31, 2017

(87) PCT Pub. No.: WO2016/124491
PCT Pub. Date: Aug. 11, 2016

(65) Prior Publication Data
US 2018/0024216 A1 Jan. 25, 2018

(30) Foreign Application Priority Data
Feb. 3, 2015 (EP) .................. 15153644

(51) Int. Cl.
*G01R 33/563* (2006.01)
*A61B 5/055* (2006.01)
(Continued)

(52) U.S. Cl.
CPC ........... *G01R 33/5635* (2013.01); *A61B 5/02* (2013.01); *A61B 5/055* (2013.01); *A61B 5/489* (2013.01);
(Continued)

(58) Field of Classification Search
CPC ............... G01R 33/56; G01R 33/5602; G01R 33/5608; G01R 33/5615; G01R 33/563;
(Continued)

(56) References Cited

U.S. PATENT DOCUMENTS

| 6,246,897 B1 * | 6/2001 | Foo | ................. G01R 33/56316 324/307 |
| 6,381,486 B1 * | 4/2002 | Mistretta | ........... G01R 33/5635 324/307 |

(Continued)

FOREIGN PATENT DOCUMENTS

JP 2010158459 A 7/2010

OTHER PUBLICATIONS

Haacke et al "Susceptibility Weighted Imaging (SWI)" Magnetic Resonance in Medicine vol. 52 (2004) p. 612-618.
(Continued)

*Primary Examiner* — Steven L Yeninas (57) ABSTRACT

Method for susceptibility weighted magnetic resonance imaging of vasculature, the method comprising the following steps: —acquiring multi-echo data containing a time-of-flight signal in at least the first echo (S1); —identifying voxels belonging to arteries from the data (S2); and—generating corresponding information on artery presence (S3); The invention further relates to a corresponding system (10) for susceptibility weighted magnetic resonance imaging of vasculature.

14 Claims, 4 Drawing Sheets

(51) Int. Cl.
*A61B 5/00* (2006.01)
*A61B 5/02* (2006.01)
*G01R 33/56* (2006.01)
*G01R 33/561* (2006.01)

(52) U.S. Cl.
CPC ...... *G01R 33/5608* (2013.01); *A61B 2576/02* (2013.01); *G01R 33/5616* (2013.01)

(58) Field of Classification Search
CPC ........ G01R 33/56308; G01R 33/56341; G01R 33/5635; G01R 33/56316; G01R 33/56366; G01R 33/5601
USPC .................. 324/306, 307, 309; 600/410, 419
IPC .......... G01R 33/56,33/5602, 33/5608, 33/5615, 33/563, 33/56308, 33/56341, 33/5635, 33/56316, 33/56366
See application file for complete search history.

(56) References Cited

U.S. PATENT DOCUMENTS

| | | | |
|---|---|---|---|
| 6,501,272 | B1 | 12/2002 | Haacke et al. |
| 6,556,856 | B1* | 4/2003 | Mistretta ............ G01R 33/5635 324/306 |
| 6,658,280 | B1* | 12/2003 | Haacke .............. A61B 5/02007 324/306 |
| 7,545,967 | B1* | 6/2009 | Prince ...................... G06T 5/50 382/130 |
| 7,917,191 | B2* | 3/2011 | Kirsch ............... G01R 33/5635 382/131 |
| 8,674,691 | B2 | 3/2014 | Du |
| 8,781,197 | B2 | 7/2014 | Wang et al. |
| 8,829,902 | B2 | 9/2014 | Yoneda et al. |
| 9,201,129 | B2* | 12/2015 | Ikedo ............... G01R 33/56545 |
| 2003/0053669 | A1* | 3/2003 | Suri ...................... G06T 7/0012 382/130 |
| 2003/0166999 | A1* | 9/2003 | Liu ........................... G06T 7/12 600/410 |
| 2003/0171671 | A1* | 9/2003 | Miyazaki ............. G01R 33/563 600/420 |
| 2009/0076374 | A1* | 3/2009 | Kimura .................. A61B 5/055 600/410 |
| 2009/0251140 | A1* | 10/2009 | Bhardwaj .......... G01R 33/5615 324/307 |
| 2010/0286504 | A1* | 11/2010 | Mistretta ............ G01R 33/4824 600/420 |
| 2011/0275926 | A1* | 11/2011 | Du ...................... G01R 33/5635 600/410 |
| 2011/0304330 | A1 | 12/2011 | Yoneda et al. |
| 2013/0293231 | A1* | 11/2013 | Hirai ...................... A61B 5/055 324/309 |
| 2015/0094563 | A1* | 4/2015 | Suwa ................... A61B 5/7285 600/413 |
| 2016/0116560 | A1 | 4/2016 | Chen et al. |

OTHER PUBLICATIONS

Gilbert et al "Complete or Partial Flow Compensation for Improved Arterial Depiction in Multi-Echo" Proceedings of the International Soc. for Magnetic Reson. in Med. Apr. 28, 2014.

Xu B et al. Flow compensated quantitative susceptibility mapping for venous oxygenation imaging, MRM vol. 72 p. 438-445 (2014).

Du YP, Jin Y. Simultaneous acquisition of MR angiography and venography (MRAV), MRM 2008; 58: 954-958.

Barnes et al "Susceptibility Weighted Imaging: Clinical Angiographic Applications" Journal of Neurological Sciences, vol. 287 p. 7-16 (2009).

* cited by examiner

METHOD AND SYSTEM FOR SUSCEPTIBILITY WEIGHTED MAGNETIC RESONANCE IMAGING

CROSS REFERENCE TO RELATED APPLICATIONS

This application is a U.S. national phase application of International Application No. PCT/EP2016/051908, filed on Jan. 29, 2016, which claims the benefit of EP Application Serial No. 15153644.8 filed on Feb. 3, 2015 and is incorporated herein by reference.

FIELD OF THE INVENTION

The invention relates to the field of susceptibility weighted imaging (SWI), more precisely to the field of susceptibility weighted imaging of venous and/or arterial vasculature. The invention especially relates to a corresponding method for SW imaging and to a corresponding MR system for SW imaging.

BACKGROUND OF THE INVENTION

Susceptibility weighted imaging (SWI) is a magnetic resonance imaging (MRI) method using a "fully flow compensated", long echo, gradient recalled echo (GRE) pulse sequence to acquire images in contrast to traditional magnetic resonance imaging using spin density, T1, or T2 imaging. A preferred version of susceptibility-weighted imaging (SWIp) realized by the applicant is based on a 4-echo multiecho gradient-echo (mFFE) sequence. 3D flow compensation is achieved for the first echo while the other echoes are flow compensated only in the readout direction. The magnitude information from the four echoes is combined using the following non-linear combination:

$$I = \sqrt[-p]{\frac{1}{N}\sum_{i=1}^{N}|S_i|^{-p}},$$

with p=2 being a typical value as described e.g. in document WO 2014/195454 A1.

Phase masking is then applied to the combined magnitude images using the PADRE algorithm (PADRE: Phase Difference Enhanced Imaging Method), which is, e.g., known from the European patent application EP 2 380 492 A1. Assuming that the vessel enhancement mode is used, the PADRE mask is defined as:

$$Mask_{PADRE}(x) = \begin{cases} e^{-\alpha(|\phi(x)|-\frac{\sigma*\pi}{100})^\beta} & \text{for } \phi \leq -\frac{\sigma*\pi}{100} \\ 1 & \text{for } \phi > -\frac{\sigma*\pi}{100} \end{cases}$$

with α=1.6, β=1.2 and σ=0 being typical values.

The fact that SWIp imaging is not fully flow-compensated will lead to blurring of the time-of-flight signal from arteries in combined SWIp images. This can however be solved by the use of a multi-echo flow compensation approach. Additionally, significant dephasing can be observed for some arteries, as a result of flow effects and accumulated phase from spin displacement in an inhomogeneous magnetic field. This makes differentiation of arterial signals from venous signals difficult.

Document WO 2009/094304 A2 describes another system and method for susceptibility weighted magnetic resonance imaging of vasculature. The system comprises a magnetic resonance device and a post-processor module. The magnetic resonance device comprises a pulse generator module configured to generate an excitation signal. The magnetic resonance device further comprises a data acquirer module communicatively coupled with the pulse generator module and configured to acquire data from at least two of the echoes. The post-processor module is communicatively coupled with the magnetic resonance device and configured to post-process the data, in particular configured to acquire MR angiography (MRA) data from at least the first echo and MR venography (MRV) data from at least the second echo.

SUMMARY OF THE INVENTION

It is an object of the invention to provide a method and a system for susceptibility weighted magnetic resonance imaging, which enable a better artery depiction.

This object is achieved by the features of the independent claims. The dependent claims detail advantageous embodiments of the invention.

According to various embodiments of the invention, the method for susceptibility weighted magnetic resonance imaging of vasculature comprises the following steps:
(a) acquiring multi-echo data containing a time-of-flight signal in at least the first echo;
(b) identifying voxels belonging to arteries from the data; and
(c) generating corresponding information on artery presence;
wherein the method further comprises an echo combination step or an echo combination step in combination with a phase masking step (S6) (d); and wherein said information on artery presence is used to guide said echo combination and/or the phase masking step.

Guiding said echo combination and/or the phase masking step should be interpreted as that said information on artery presence is used to put emphasis on an artery appearance during said echo combination and/or to prevent an inclusion of voxels belonging to arteries in the phase masking step. By preventing inclusion of voxels belonging to arteries in the phase masking step the inclusion of unreliable phase information is prevented. In the echo combination step the magnitude information from the echoes is combined. Preferably, the multi echo is a 4-echo gradient-echo.

The invention is based on the basic idea to include information about the location of arteries into the echo combination and phase masking steps that are part of the normal processing to generate a multi-echo susceptibility weighted image. This information about the location of the arteries can be extracted from the multi-echo acquisition itself.

The method ensures an optimization of multi-echo susceptibility weighted imaging for an improved differentiation between arteries and veins.

There are different suitable mask types for performing the phase masking step. The various types of masks differ by the mathematical expressions that are being used to compute them from the phase data and any mathematical expression could in theory be modified to include information about the presence of arteries. The information about the location of arteries can be included into many of these mask types. One of the most frequently used type of mask is a linear phase mask known from the scientific paper >>E. Haacke et al.: "Susceptibility Weighted Imaging (SWI)"; Magnetic Resonance in Medicine 52:612-618 (2004)<<, which is then multiplied several times. This type of mask can easily be adapted for performing the phase masking step of the method for susceptibility weighted magnetic resonance imaging of vasculature.

Within each corresponding multi-echo pulse sequence an excitation signal, a first echo, and at least one further echo occur during the repetition time. The data acquisition is a data acquisition from the first echo and at least one further echo (second echo, . . . ) and further includes at least the time-of-flight signal of the first echo. Preferably, more than two echoes occur during the repetition time. According to a preferred embodiment of the invention, 3D flow compensation is achieved for all echoes.

According to another preferred embodiment of the invention, the voxels belonging to arteries are identified in an image based on early echo data. Arteries can be reliably identified in the early echo images as a result of their bright time-of-flight signal. Given that arteries are relatively thin structures, an arterial image (AI) can be created using the following approach:

$$AI = \frac{|I_{Echo1}|}{\langle|I_{Echo1}|\rangle} - 1, AI(AI < 0) = 0, AI(AI > 1) = 1$$

wherein $I_{Echo1}$ is a magnitude signal from the first echo or a combination of the first few echoes and $|\langle I_{Echo1}\rangle|$ is a low-pass filtered version of the magnitude signal from the first echo or a combination of the first few echoes.

Alternatively, arteries can also be identified by looking at voxels for which the phase evolution as a function of TE (TE: echo time) is not linear. This indicates that the phase in these voxels is not dominated by susceptibility effects, but rather by other mechanisms (mainly flow).

The combination algorithm can then be modified to put emphasis on the earlier echoes for voxels where the AI is high:

$$I = \sqrt[-p]{\frac{1}{N}\sum_{i=1}^{N}|S_i|^{-p}}, \text{ with } p = \begin{cases} r\left(1 - \frac{AI}{2t}\right) & \text{for } AI \leq t \\ r\left(\frac{1-AI}{2(1-t)}\right) & \text{for } AI > t \end{cases}$$

wherein p is an integer, or non-integer greater than zero, r is a weighting factor from different echoes, and t is a threshold value that separates voxels that are unlikely to contain arteries from voxel that are likely to contain arteries. Using this combination, p→r when AI→0, which corresponds to voxels that are unlikely to contain arteries. Inversely, p→−r when AI→1, which corresponds to voxels that are very likely to contain arteries. The threshold value t marks the limit between the two regimens.

According to yet another preferred embodiment of the invention the PADRE phase masking algorithm is modified to avoid masking voxels where AI is high:

$$Mask_{PADRE}(x) = \begin{cases} e^{-\alpha[(1-AI)^\delta(|\phi(x)|-\frac{\sigma*\pi}{100})]^\beta} & \text{for } \phi \leq -\frac{\sigma*\pi}{100} \\ 1 & \text{for } \phi > -\frac{\sigma*\pi}{100} \end{cases}$$

wherein α, β and σ are variables that control the response function of the $MASK_{PADRE}(x)$, δ is a weighting factor that controls the importance of the arterial term of the $MASK_{PADRE}(x)$, and φ(x) is the phase of the signal.

According to various embodiments of the invention a computer program product is supposed to execute the method steps of the aforementioned method. The computer program product could be a program to control an MRI device. The computer program product could also be configured to be a stand-alone product, which could for example be executed on a computer. In case the computer program product is configured as a stand-alone product, the computer program product is configured to use multi-echo data containing a time-of-flight signal in at least the first echo as an input (instead of being configured to acquire those data). Further the computer program product could be configured to perform all method steps and combinations thereof as disclosed herein.

According to various embodiments of the invention, the corresponding system for susceptibility weighted magnetic resonance imaging of vasculature comprises the following components:

a magnetic resonance device comprising
a pulse generator module configured to generate an excitation signal (excitation pulse); and
a data acquirer module, communicatively coupled with the pulse generator module and configured to acquire multi-echo data containing a time-of-flight signal in at least the first echo; and
a post-processor module, communicatively coupled with the magnetic resonance device and configured
to post-process the data including an echo combination step and/or a phase masking step,
to identify voxels belonging to arteries from the data; and
to generate corresponding information on artery presence;
wherein said information on artery presence is used to guide the echo combination and/or phase masking step.

According to another preferred embodiment of the invention the system for susceptibility weighted magnetic resonance imaging is configured to perform the aforementioned method for susceptibility weighted magnetic resonance imaging.

The system ensures an optimization of multi-echo susceptibility weighted imaging for an improved differentiation between arteries and veins.

According to preferred embodiment of the invention, the voxels belonging to arteries are identified in an image based on first echo data or a combination of the first few echoes.

According to another preferred embodiment of the invention the post-processor module is configured to generate an image of the vasculature from the post-processed data.

According to yet another preferred embodiment of the invention, the system further comprises a display generator module, communicatively coupled with the post-processor module and configured to display the image of the vasculature generated from the post-processed data.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

In the following discussion reference is made to arterial tissue as the object to be imaged. The invention is however applicable to other tissue as well. The arterial tissue is selected merely as a preferred example.

Figure 1:
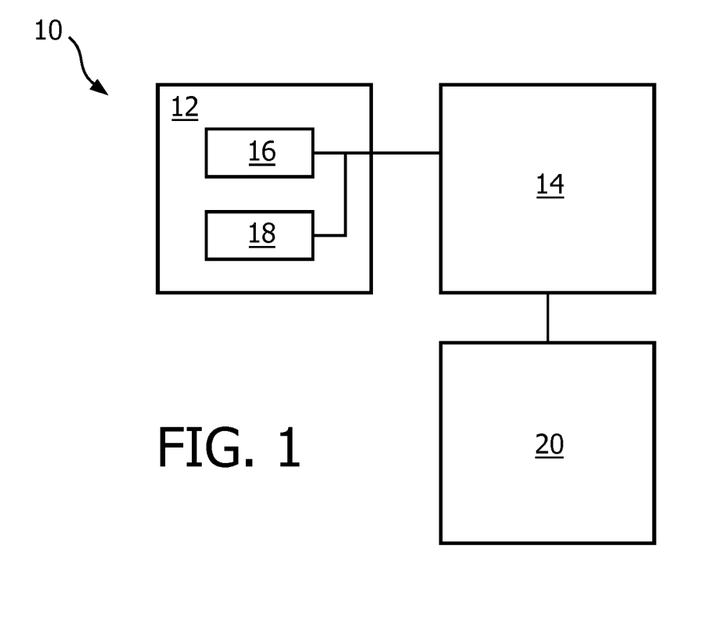
FIG. 1 shows a schematic representation of a system for susceptibility weighted magnetic resonance imaging according to a preferred embodiment of the invention.

FIG. 1 shows a schematic representation of a system 10 for susceptibility weighted magnetic resonance imaging. The system 10 comprises two main components, namely a magnetic resonance device 12 and a post-processor module 14. The magnetic resonance device 12 comprises a pulse generator module 16 configured to generate an initial excitation signal, and a data acquirer module 18, communicatively coupled with the pulse generator module 16 and configured to acquire multi-echo data containing a time-of-flight signal in at least the first echo. The post-processor module 14 is communicatively coupled with the magnetic resonance device 12 and configured (i) to post-process the data including an echo combination step and a phase masking step, (ii) to identify voxels belonging to arteries from the data; (iii) to generate corresponding information on artery presence, wherein said information on artery presence is used to guide the echo combination and/or phase masking step, and (iv) to generate an image of the vasculature from the post-processed data. The system 10 further comprises a display generator module 20, communicatively coupled with the post-processor module 14 and configured to display the image of the vasculature generated from the post-processed data.

Figure 2:
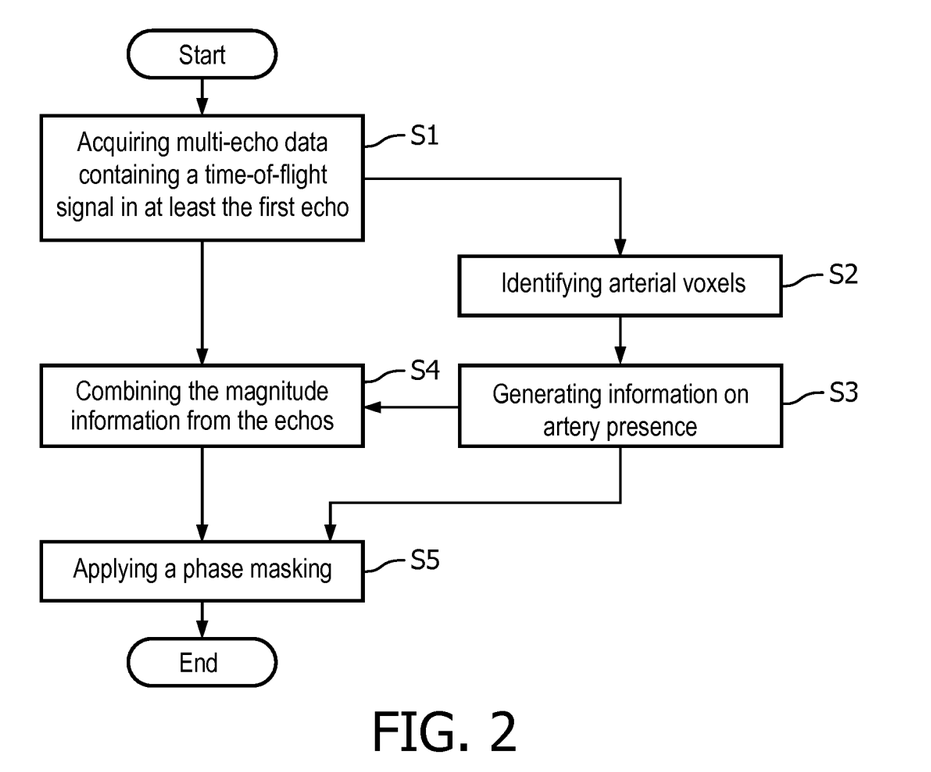
FIG. 2 shows a flow chart of a process for susceptibility weighted magnetic resonance imaging according to preferred embodiments of the invention.

FIG. 2 shows a flow chart of a process for susceptibility weighted magnetic resonance imaging of vasculature. The process comprises the following steps:

Step 1 (S1): acquiring multi-echo data containing a time-of-flight signal in at least the first echo;

Step 2 (S2): identifying voxels belonging to arteries from an image based on first echo data or a combination of the first few echoes; and Step 3 (S3): generating corresponding information on artery presence;

Step 4 (S4): combining the magnitude information from the echoes by use of a non-linear combination; and Step 5 (S5): applying a phase masking to the combined magnitude images generated in Step 4 using a suitable mask like e.g. the PADRE mask of the PADRE algorithm, wherein said information on artery presence (generated in step 3) is used to guide said echo combination step S4 and/or the phase masking step S5. In a final step at the end, an image of the vasculature is generated from the post-processed data resulting from steps 4 and 5.

Figure 3A:
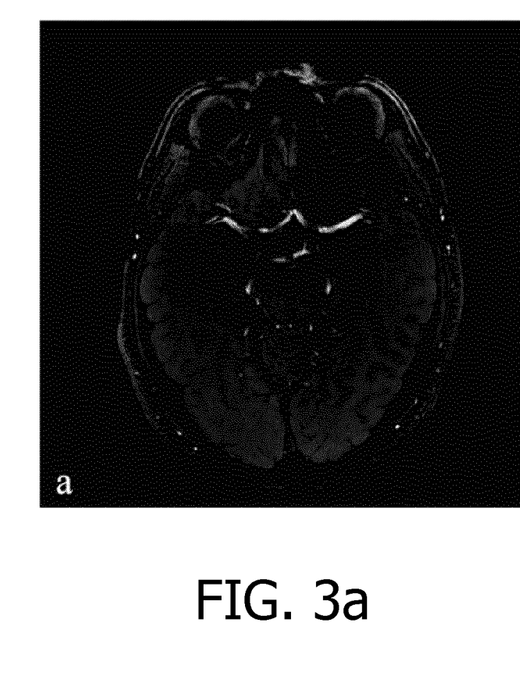
FIGS. 3a and 3b show two arterial images (AIs) for identifying voxels belonging to arteries.
Figure 3B:
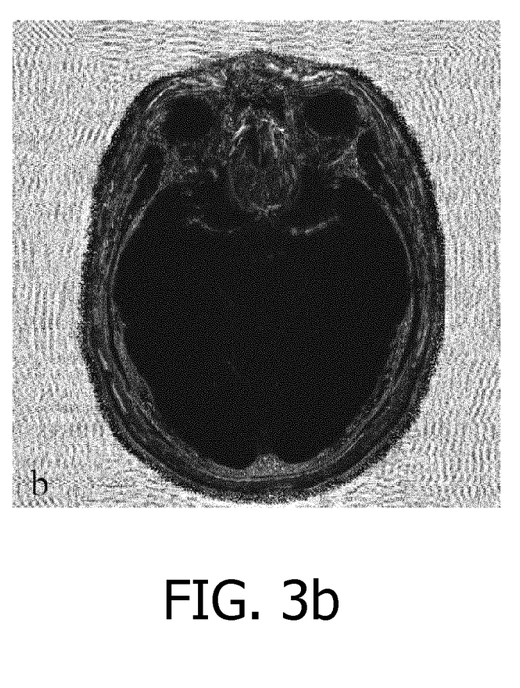

FIGS. 3a and 3b show two images for identifying voxels belonging to arteries (AIs: arterial images). The arteries can be identified by use of the information from the first echo or a combination of the first few echoes to create an arterial image (AI) (FIG. 3a on the left side), or by calculating a normalized residual of the linear fit of the phase as a function of the echo time (FIG. 3b on the right side).

Figure 4:
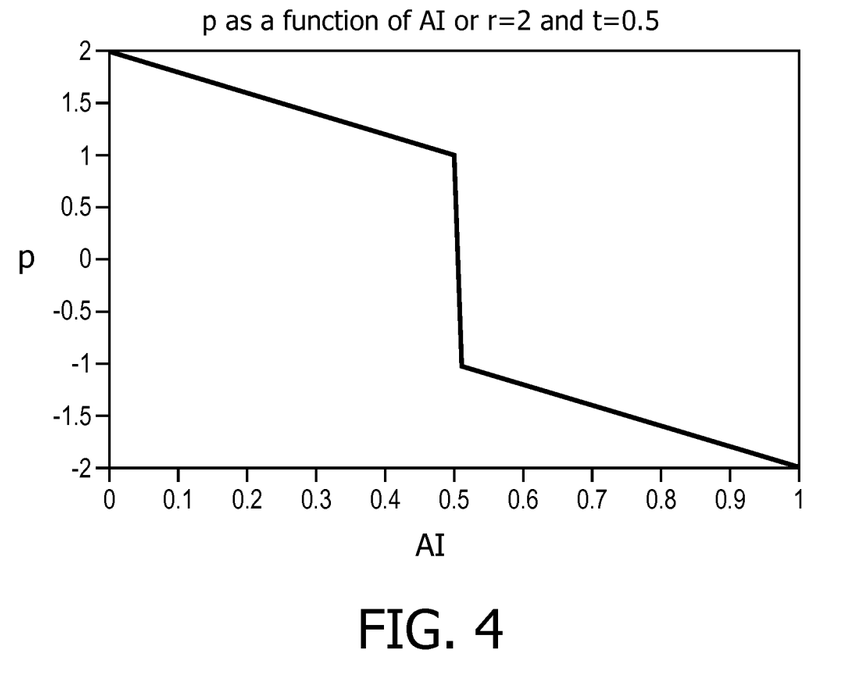
FIG. 4 shows a diagram depicting the variable p as a function of the arterial image AI.

FIG. 4 shows a diagram depicting the variable p as a function of the arterial image AI according to the equation:

$$p = \begin{cases} r\left(1 - \frac{AI}{2t}\right) & \text{for } AI \leq t \\ r\left(\frac{1-AI}{2(1-t)} - 1\right) & \text{for } AI > t \end{cases}$$

for r=2 and t=0.5. The parameter p is used to combine the magnitude information from the four echoes using the non-linear combination:

$$I = \sqrt[-p]{\frac{1}{N}\sum_{i=1}^{N}|S_i|^{-p}}.$$

Figure 5A:
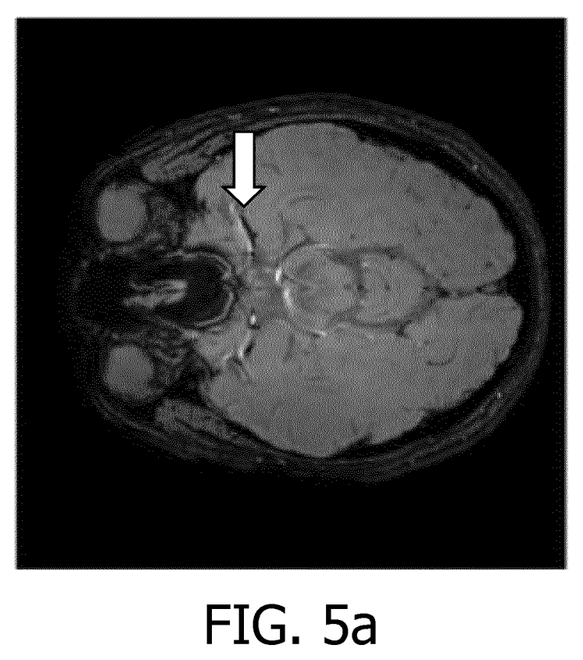
FIGS. 5a and 5b show two susceptibility weighted images processed by use of different susceptibility weighted magnetic resonance imaging processes.
Figure 5B:
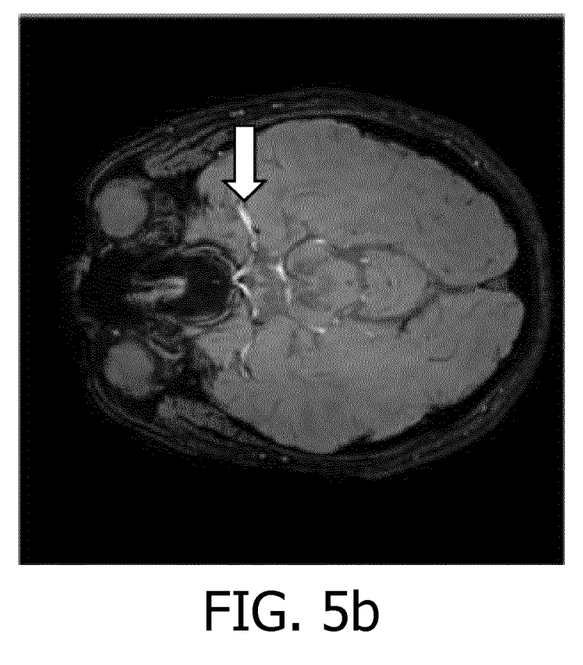

The FIGS. 5a and 5b show two susceptibility weighted images of the same human head. The SWIp image shown in FIG. 5a is processed by use of the susceptibility weighted magnetic resonance imaging process known from the prior art, which is based on the 4-echo multiecho gradient-echo (mFFE) sequence. The image shown in FIG. 5b is processed by use of the susceptibility weighted magnetic resonance imaging process described in FIG. 2. As indicated by the FIGS. 5a and 5b: by using the process depicted in FIG. 2 a better differentiation between arteries and veins can be made.

The use of the proposed combination and phase masking algorithms effectively restores the bright time-of-flight signal even in the largest arteries, thus providing a more reliable differentiation between arteries and veins. The very good susceptibility contrast provided by the SWIp sequence is effectively preserved for all voxels where the AI signal is low.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for susceptibility weighted magnetic resonance imaging of vasculature, the method comprising:
    acquiring multi-echo data containing a time-of-flight signal in at least a first echo;
    identifying voxels belonging to arteries from the multi-echo data; and
    generating corresponding information on artery presence;
    performing an echo combination step, or an echo combination step in combination with a phase masking step;
    using said corresponding information on artery presence to put emphasis on an artery appearance during said echo combination step and to prevent an inclusion of voxels belonging to arteries in the phase masking step;

creating an arterial image AI; and identifying the voxels belonging to arteries in said arterial image, wherein in the performing the echo combination step, magnitude information from the echoes is combined using the following non-linear combination:

$$I = -\sqrt[p]{\frac{1}{N}\sum_{i=1}^{N}|S_i|^{-p}}, \text{ with}$$

$$p = \begin{cases} r\left(1 - \frac{AI}{2t}\right) \text{for } AI \leq t \\ r\left(\frac{(1-AI)}{2(1-t)}\right) \text{for } AI > t \end{cases}$$

wherein p is an integer or a non-integer greater than zero, r is a weighting factor from different echoes, and t is a threshold value that separates voxels that are unlikely to contain arteries from voxel that are likely to contain arteries.

2. The method according to claim 1, further comprising creating the arterial image AI by using first echo data or a combination of a first few echoes, or by determining a normalized residual of a linear fit of phase as a function of echo time.

3. The method according to claim 2, wherein the creating the arterial image AI comprises determining AI as follows:

$$AI = \frac{|I_{Echo1}|}{\langle|I_{Echo1}|\rangle} - 1, AI(AI < 0) = 0, AI(AI > 1) = 1,$$

wherein $I_{Echo1}$ is a magnitude signal from the first echo or the combination of the first few echoes and $|\langle I_{Echo1}\rangle|$ is a low-pass filtered version of the magnitude signal from the first echo or the combination of the first few echoes.

4. The method according to claim 1, further comprising identifying arteries by determining voxels for which a phase evolution as a function of echo time is not linear.

5. The method according to claim 1, further comprising applying the phase masking step to combined magnitude images using the PADRE algorithm.

6. The method according to claim 5, wherein a Padre mask of the PADRE algorithm is defined as:

$$Mask_{PADRE}(x) = \begin{cases} e^{-\alpha[(1-AI)^\delta(|\phi(x)|-\frac{\sigma*\pi}{100})]^\beta} & \text{for } \phi \leq -\frac{\sigma*\pi}{100} \\ 1 & \text{for } \phi > -\frac{\sigma*\pi}{100} \end{cases}$$

wherein α, β and σ are variables that control a response function of the $MASK_{PADRE}(x)$, δ is a weighting factor that controls an importance of an arterial term of the $MASK_{PADRE}(x)$, and φ(x) is the phase of the signal.

7. A non-transitory computer readable medium storing instructions that, when executed by a processor, cause the processor to perform a method comprising:

identifying voxels belonging to arteries from multi-echo data containing a time-of-flight signal in at least a first echo;

generating corresponding information on artery presence;

performing an echo combination step or an echo combination step in combination with a phase masking step; and using said corresponding information on artery presence to put emphasis on an artery appearance during said echo combination step and to prevent an inclusion of voxels belonging to arteries in the phase masking step;

create an arterial image AI; and identify the voxels belonging to arteries in the arterial image, wherein in the performing the echo combination step, magnitude information from the echoes is combined using the following non-linear combination:

$$I = -\sqrt[p]{\frac{1}{N}\sum_{i=1}^{N}|S_i|^{-p}}, \text{ with}$$

$$p = \begin{cases} r\left(1 - \frac{AI}{2t}\right) \text{for } AI \leq t \\ r\left(\frac{(1-AI)}{2(1-t)}\right) \text{for } AI > t \end{cases}$$

wherein p is an integer or a non-integer greater than zero, r is a weighting factor from different echoes, and t is a threshold value that separates voxels that are unlikely to contain arteries from voxel that are likely to contain arteries.

8. The non-transitory computer readable medium of claim 7, wherein the instructions, when executed by a processor, further cause the processor to create an arterial image AI by using first echo data or a combination of a first few echoes, or by determining a normalized residual of a linear fit of phase as a function of an echo time.

9. The non-transitory computer readable medium according to claim 8, wherein the instructions, when executed by a processor, further cause the processor to the arterial image AI by determining AI as follows:

$$AI = \frac{|I_{Echo1}|}{\langle|I_{Echo1}|\rangle} - 1, AI(AI < 0) = 0, AI(AI > 1) = 1,$$

wherein $I_{Echo1}$ is a magnitude signal from the first echo or a combination of a first few echoes and $|\langle I_{Echo1}\rangle|$ is a low-pass filtered version of the magnitude signal from the first echo or a combination of the first few echoes.

10. A system for susceptibility weighted magnetic resonance imaging of vasculature, the system comprising:

a magnetic resonance device comprising:
  a pulse generator module configured to generate an excitation signal; and
  a data acquirer module, communicatively coupled with the pulse generator module and configured to acquire multi-echo data containing a time-of-flight signal in at least a first echo; and
  a post-processor module, communicatively coupled with the magnetic resonance device and configured:
  to post-process the multi-echo data including an echo combination step and a phase masking step,
  to identify voxels belonging to arteries from the multi-echo data;
  to generate corresponding information on artery presence, wherein said corresponding information puts emphasis on an artery appearance during said echo combination step and prevents an inclusion of voxels belonging to arteries in the phase masking step;

create an arterial image AI;

identity the voxels belonging to arteries in the arterial image; and determine magnitude information from the echoes is combined using the following non-linear combination:

$$I = -\sqrt[p]{\frac{1}{N}\sum_{i=1}^{N}|S_i|^{-p}}, \text{ with}$$

$$p = \begin{cases} r\left(1 - \frac{AI}{2t}\right) \text{for } AI \leq t \\ r\left(\frac{(1-AI)}{2(1-t)}\right) \text{for } AI > t \end{cases}$$

wherein p is an integer or a non-integer greater than zero, r is a weighting factor from different echoes, and t is a threshold value that separates voxels that are unlikely to contain arteries from voxel that are likely to contain arteries.

11. The system according to claim 10, wherein the post-processor module is further configured to generate an image of vasculature from the post-processed multi-echo data.

12. The system according to claim 10, further comprising a display generator module communicatively coupled with the post-processor module and configured to display an image of vasculature generated from the post-processed multi-echo data.

13. The system according to claim 10, wherein the post-processor module is further configured to create arterial image AI by using first echo data or a combination of a first few echoes, or by determining a normalized residual of a linear fit of phase as a function of an echo time.

14. The system according to claim 13, wherein the post-processor module is further configured to determine the arterial image AI as follows:

$$AI = \frac{|I_{Echo1}|}{\langle I|_{Echo1}|\rangle} - 1, AI(AI < 0) = 0, AI(AI > 1) = 1$$

wherein $I_{Echo1}$ is a magnitude signal from the first echo or a combination of a first few echoes and $|\langle I_{Echo1}\rangle|$ is a low-pass filtered version of the magnitude signal from the first echo or a combination of the first few echoes.

* * * * *